United States Patent [19]
Del Rio et al.

[11] Patent Number: 5,741,084
[45] Date of Patent: Apr. 21, 1998

[54] WEAR COMPENSATING AXIAL CONNECTION

[76] Inventors: Eddy H. Del Rio, 11413 52nd Rd., Royal Palm Beach, Fla. 33411; William E. Anspach, Jr., 4500 Riverside Dr., Palm Beach Gardens, Fla. 33410

[21] Appl. No.: 784,476

[22] Filed: Jan. 17, 1997

Related U.S. Application Data

[63] Continuation of Ser. No. 410,980, Mar. 27, 1995, abandoned.

[51] Int. Cl.$^6$ .................................. F16B 7/20; A61B 17/56
[52] U.S. Cl. .................. 403/349; 285/361; 285/376; 285/396; 285/402; 403/315; 433/126; 604/283; 606/1
[58] Field of Search .................... 285/360, 361, 285/376, 377, 396, 401, 402; 403/315, 349; 433/126; 604/283; 606/1, 80, 170, 180

[56] References Cited

U.S. PATENT DOCUMENTS

| | | | |
|---|---|---|---|
| 617,591 | 1/1899 | Miller et al. | 285/361 X |
| 744,589 | 11/1903 | Moore | 285/376 X |
| 828,243 | 8/1906 | Polmann | 285/376 X |
| 920,188 | 5/1909 | Schumacher | 403/349 X |
| 931,327 | 8/1909 | Manzel | 403/349 X |
| 1,029,819 | 6/1912 | Nylander | 285/376 X |
| 1,033,187 | 7/1912 | Metzger | 403/349 X |
| 1,038,948 | 9/1912 | Patrick | 285/361 X |
| 1,099,670 | 6/1914 | Shoffner | 403/349 X |
| 1,333,342 | 3/1920 | Robertson et al. | 403/349 X |
| 1,871,421 | 8/1932 | Muhlhauser et al. | 285/361 X |
| 2,076,918 | 4/1937 | Robison | 285/396 X |
| 2,315,981 | 4/1943 | Olson | 285/402 X |
| 2,648,553 | 8/1953 | Ulrich | 285/361 X |
| 2,710,000 | 6/1955 | Cromer et al. | 606/180 X |
| 3,455,580 | 7/1969 | Howard | 285/396 X |
| 5,397,196 | 3/1995 | Boiret et al. | 403/349 X |
| 5,466,020 | 11/1995 | Page et al. | 285/361 |

FOREIGN PATENT DOCUMENTS

| | | | |
|---|---|---|---|
| 2002476 | 2/1979 | United Kingdom | 433/126 |

*Primary Examiner*—Kenneth J. Dorner
*Assistant Examiner*—Andrea Chop
*Attorney, Agent, or Firm*—Jack N. McCarthy

[57] ABSTRACT

A surgical instrument has a motor housing with a cylindrical member extending therefrom and has a pin projecting radially from the cylindrical member. A nose piece removably attached to the housing has a circular aperture which receives the cylindrical member and which has a channel within which the pin slides during attachment and removal. The nose piece includes a cantilevered arcuate spring arm that urges the pin along the channel toward a position at which the pin is wedged against a wall of the channel to force the nose piece into an operating engagement with the motor housing and retains the pin in the channel resisting detachment.

14 Claims, 4 Drawing Sheets

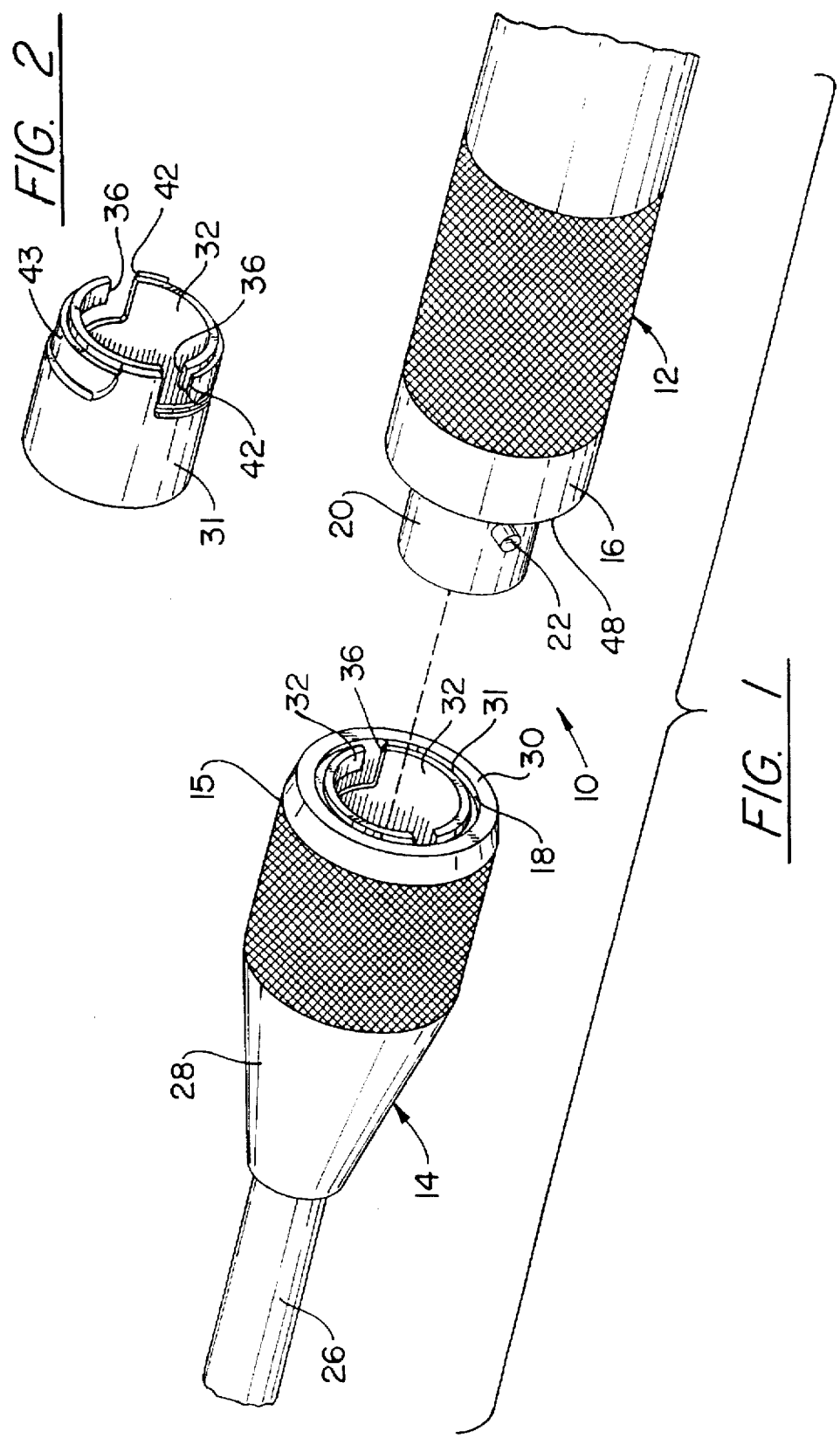

WEAR COMPENSATING AXIAL CONNECTION

This is a continuation of application Ser. No. 08/410,980 filed on Mar. 27, 1995, now abandoned.

DESCRIPTION

The present invention relates to motor driven surgical instruments, and specifically to mechanisms for releasably attaching a variety of different tool bits to the surgical instrument.

BACKGROUND ART

Orthopedic and neurological surgeons frequently use a power driven surgical instrument to cut, shape and drill into bone. Such an instrument utilizes a small pneumatically driven motor contained in a cylindrical housing which is held by the surgeon during use. A hose from the source of compressed air attaches to one end of the cylindrical housing. A tool bit is received by a fitting at the other end of the housing and is rotated by the motor when compressed air is applied to the instrument. A wide variety of different shaped and sized tool bits is available as needed during a surgical procedure. Thus, the surgical instrument must be able to accept various kinds and sizes of tool bits.

One surgical instrument of this type had a tapered tubular nose piece that screwed onto one end of the motor housing. The shaft of a tool bit was inserted through the aperture of the nose piece and engaged the motor shaft within the housing. Because various tool bits had different sized shafts, different size nose pieces had to be provided. Replacement of the nose piece required a wrench and was time consuming and cumbersome in an operating room environment. Further, the wrench had to be accounted for before and after the procedure and sterilized between procedures, which amounted to additional work.

Because these surgical instruments rotate at speeds which reach 80,000 RPM, the nose piece had to be accurately aligned on the motor housing to prevent flexing of the tool bit shaft. The threaded attachment provided that accurate alignment and secured those components against vibrational movement with respect to each other.

Although bayonet connecting mechanisms are well known for connecting similar components, conventional mechanisms of that type were not secure enough when subjected to the vibration at such high speeds. Even when closely toleranced bayonet fastening mechanisms were utilized, wear from repeated attachment and removal of the nose piece from the motor housing eventually permitted movement between the nose piece and the motor housing. Even relatively small movement can have serious adverse effects at the high rotational speed of the tool bit.

DISCLOSURE OF INVENTION

The general object of the present invention is to provide a mechanism for securely attaching a removable nose piece to a motor housing of a surgical instrument.

Another object is to provide such an attachment mechanism which does not require the use of wrenches or other tools to change the nose piece.

A further object of the present invention is to provide a mechanism for securely attaching a nose piece to a motor housing of a surgical instrument which compensates for wear of the components.

These objects are fulfilled by a wear compensating connector assembly wherein the motor housing has a cylindrical projection with two pins extending radially therefrom at diametrically opposed points. The nose piece has an aperture having an inner and outer sleeve fixed therein with the inner sleeve having two channels for receiving said pins, said outer sleeve against the wall of said aperture providing a spring action to hold the pins in place. When the cylindrical projection is inserted into the sleeves fixed in the aperture, each pin is received in an open end of its cooperating channel. Preferably, each channel has a first portion extending axially inwardly from the connecting end of the nose piece and a second portion extending circumferentially and angularly away from the connecting end of the nose piece.

Two cantilevered arcuate spring arms are provided on the second sleeve at the connecting end of the nose piece for urging the pins along the channels of the first sleeve toward a wedged position with the nose piece. At that position the cantilevered arcuate spring arms also act to retain the pins in the channels.

In the preferred implementation of the present invention, the nose piece has a body with an aperture which receives a first inner and a second outer concentric sleeve. Each sleeve has two generally L-shaped channels extending inward from one end. The channels of the first sleeve maintain a constant width for guiding the pins. The sides of these channels between the pins and the connecting ends of the nose piece and motor housing provide a ramp to achieve a wedging action along the ramp as the pins are moved to a final state of attachment. The channels of the second sleeve permit the guided movement of the pins in the channels of the first sleeve. Each cantilevered arcuate spring arm forms one side of each channel in the second sleeve and has a triangular projection extending into the channel over the ramp to cooperate with each pin to hold the pins in place when the nose piece and motor housing are attached.

Each triangular projection of said cantilevered arcuate spring arm has a flat side, for being contacted by a cooperating pin starting down the circumferential second portion of its cooperating channel in the first guiding sleeve, and a curved side forming an apex, each apex contacting each cooperating pin when it has passed over the top of the flat side providing a force acting against each pin to hold it in position. Each curved surface has a radius matching the radius of each cooperating pin to receive the pin when the connector has reached the end of its useful life.

Each cantilevered arcuate spring arm is made thinner than the rest of the second outer sleeve to permit the spring arm to move axially between the first inner guiding sleeve and the inner wall of the aperture in the nose piece to provide the spring action.

When the nose piece and the motor housing first reach a final state of attachment, each pin has passed over the apex of its cooperating triangular projection and the top of each curved side provides a force acting on its cooperating pin.

BRIEF DESCRIPTION OF THE DRAWINGS

FIG. 1 is an exploded illustration of a motor housing and coupling nose piece of a surgical instrument according to the present invention;

FIG. 2 is an isometric view of a bayonnet connector showing the inner guide sleeve and an outer securing spring sleeve in the nose piece of FIG. 1;

BEST MODE FOR CARRYING OUT THE INVENTION

Figure 3:
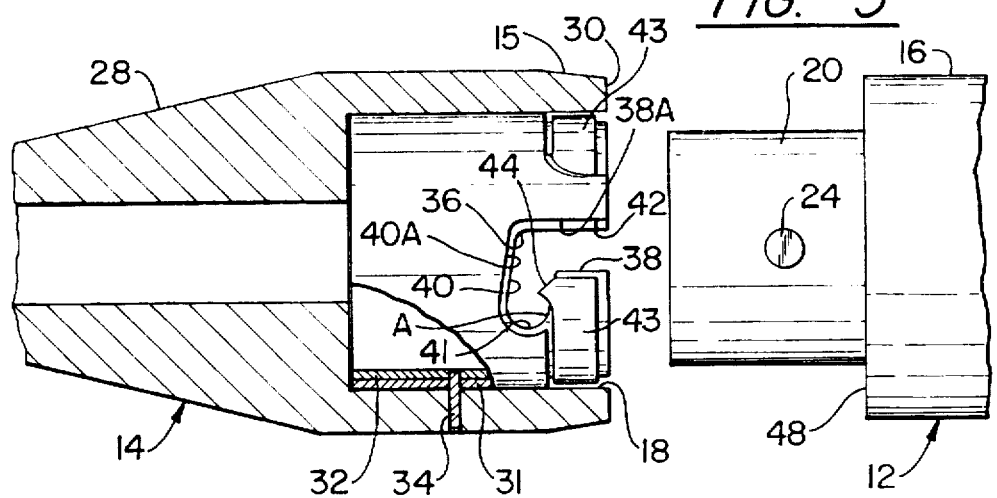
FIG. 3 is a view partially in section showing the nose piece aligned with an end of the motor housing prior to attachment.

Referring initially to FIG. 1, a surgical instrument 10 that incorporates the present invention has a motor housing 12 which enclosed a pneumatic motor. A removable nose piece 14 is attached to one end 16 of the motor housing 12 and has a longitudinal aperture 18 that receives a shaft of an interchangeable tool bit (not shown) which extends into the motor housing 12 so as to be driven by the motor. Various types of tool bits have different size shafts and require a correspondingly sized nose piece 14 to be attached to the end 16 of the housing 12.

The attachment of the nose piece 14 to the motor housing 12 is accomplished by a bayonet connector assembly. The connector assembly has a cylindrical, tubular extension 20 projecting from end 16 of the motor housing 12 forming an annular flange surface 48 on the motor housing 12. Two diametrically opposed pins 22 and 24, with only pin 22 being visible in FIG. 1, project radially along a common line from opposite sides of the tubular extension 20. When a tool bit is inserted in the surgical instrument 10, the tool bit shaft extends through the tubular extension 20 into the motor housing 12 and engages a coupling on the internal motor.

Surgical instrument nose piece 14 has a tool support tube 26 connected to one end of a body 28 which has a circular opening 48 in a flat end surface 30 at the other connecting end 15. A pair of concentric cylindrical sleeves 31 and 32 are located in the opening 18 of the nose piece 14. Specifically, inner sleeve 32 has a tight fit in outer sleeve 34 which in turn has a tight fit in opening 48. As shown in FIG. 3, a fastening pin 34 extends through a radial hole in the body 28 of the nose piece 14 and through holes in the two sleeves 31 and 32 to hold that combination together in a fixed alignment which will be apparent from the following description.

With reference to FIGS. 2 and 3, inner sleeve 32 has a pair of channels, or slots, 36 extending inwardly from an exposed end of the sleeve 32. Sleeve 32 extends approximately to connecting end surface 30 of the nose piece 44. The channels 36 are diametrically positioned on opposite sides of the inner sleeve 32 so as to receive, and guide, pins 22 and 24 when the nose piece 44 is assembled onto motor housing 12. Each channel 36 is generally L-shaped being formed by two adjoining channel portions 38 and 40. Specifically, the first channel portion 38 has an open end formed in the exposed end of inner sleeve 32 and then extends longitudinally along the inner sleeve 32. The second channel portion 40 extends circumferentially around the sleeve 32 at an angle of approximately 100° from the inner end of the first channel portion 38 and terminates at a closed end 41. The second channel portion 40 of each channel 36 is closer to the end surface 30 of the nose piece 14 at the junction with the first channel portion 38 than at the closed end 41. As will be described, this angling of the second channel portion 40 away from the end surface 30 forms a ramp A at the side of channel, or slot, 36 which is closest to the end surface 30 which draws the nose piece 14 against the motor housing 12 as the pins 22 and 24 slide along the ramp A of the second portions 40 of channels 36 during assembly. The distance between the ramp A of the channel 36 closest to the closed end 41, and the end surface 30 of the nose piece 14 is greater than the distance between the pins 22, 24 and flange surface 48 around tubular extension 20 at the end 16 of the motor housing 12. This distance relationship ensures that ramp A of the inner sleeve 32 will be wedged between pins 22, 24 and the flange surface 48 with surfaces 30 and 48 abutting when the nose piece 14 is properly attached to the motor housing 12. This connection will be further discussed hereinafter.

Outer sleeve 31 has a similar pair of generally L-shaped channels, or slots, 42 formed therein and located substantially radially in line with channels 36 in the inner sleeve 32, so as not to interfere with the movement of pins 22 and 24 in channels 36 when the two sleeves are fastened within the nose piece 14 by fastening pin 34. Each channel 42 is formed with a first wall portion 38A that is not aligned with the wall 38 of channel 36 and extends longitudinally outside of the wall 38 into the outer sleeve 31, and a second wall portion 40A that extends circumferentially outside of the longer wall of second portion 40 of channel 36 and outside of closed end 41. The outer sleeve 31 includes a pair of cantilevered arcuate spring arms 43 formed at its connecting end.

Each cantilevered arcuate spring arm 43 extends from a solid portion 45 of the connecting end of sleeve 31 near one channel 36 to an end 51 just short of the other channel 36. The end 51 of each cantilevered arcuate spring arm 43 forms, with the wall portion 38A, the longitudinal portion of the generally L-shaped channel 42. Each cantilevered arcuate spring arm 43 is spaced from the fixed circumference of the sleeve 31 on its inner side by a slit, or straight narrow cut, 50 and extends at 53 to form with wall portion 40A the circumferential portion of the generally L-shaped channel 42, and the outer side of each cantilevered arcuate spring arm 43 is spaced inwardly from the outer end of the end surface 30 of the nose piece 14 to allow for its full spring movement. Each cantilevered arcuate spring arm 43 is made thinner than the rest of the second outer sleeve 31, from line B to its end 51, to permit the spring arm to move freely in an axial direction between the first inner guiding sleeve 32 and the inner wall of aperture 18. This space permits any twisting of cantilevered arcuate spring arm 43 to occur, as it is moved axially, without restricting the spring action. The free end of each cantilevered arcuate spring arm 43 has a triangular projection 44 that projects into the adjacent channel 42 in the outer sleeve 31 and over the ramp A of the channel portion 40 of channel 36. Each triangular projection 44 has a straight cam surface 55 and a curved holding, or securing, surface 60 which will be hereinafter described.

Figure 6:
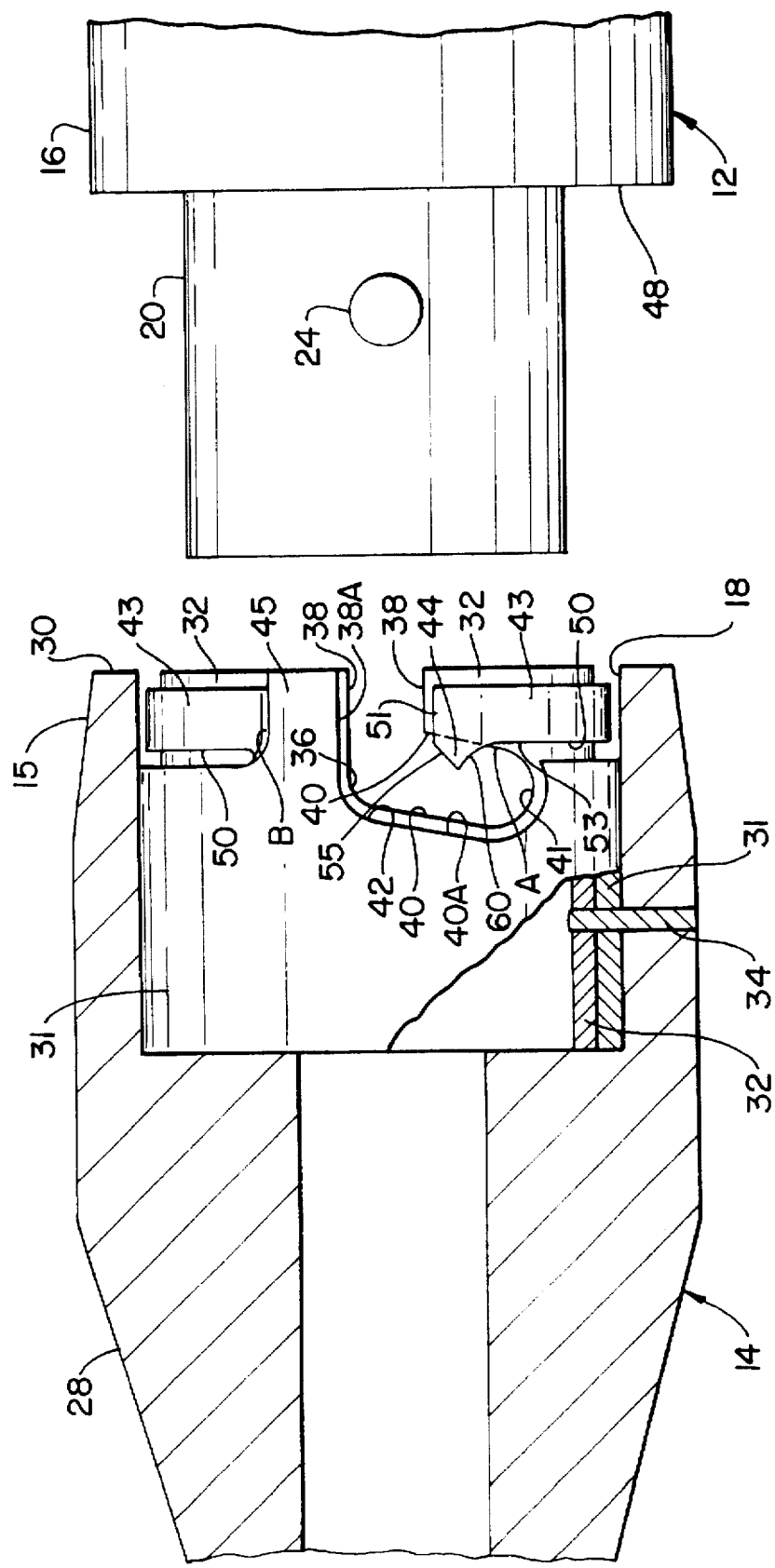
FIG. 6 is an enlarged view of the bayonet connector prior to attachment with parts of the outer securing spring sleeve broken away.
Figure 7:
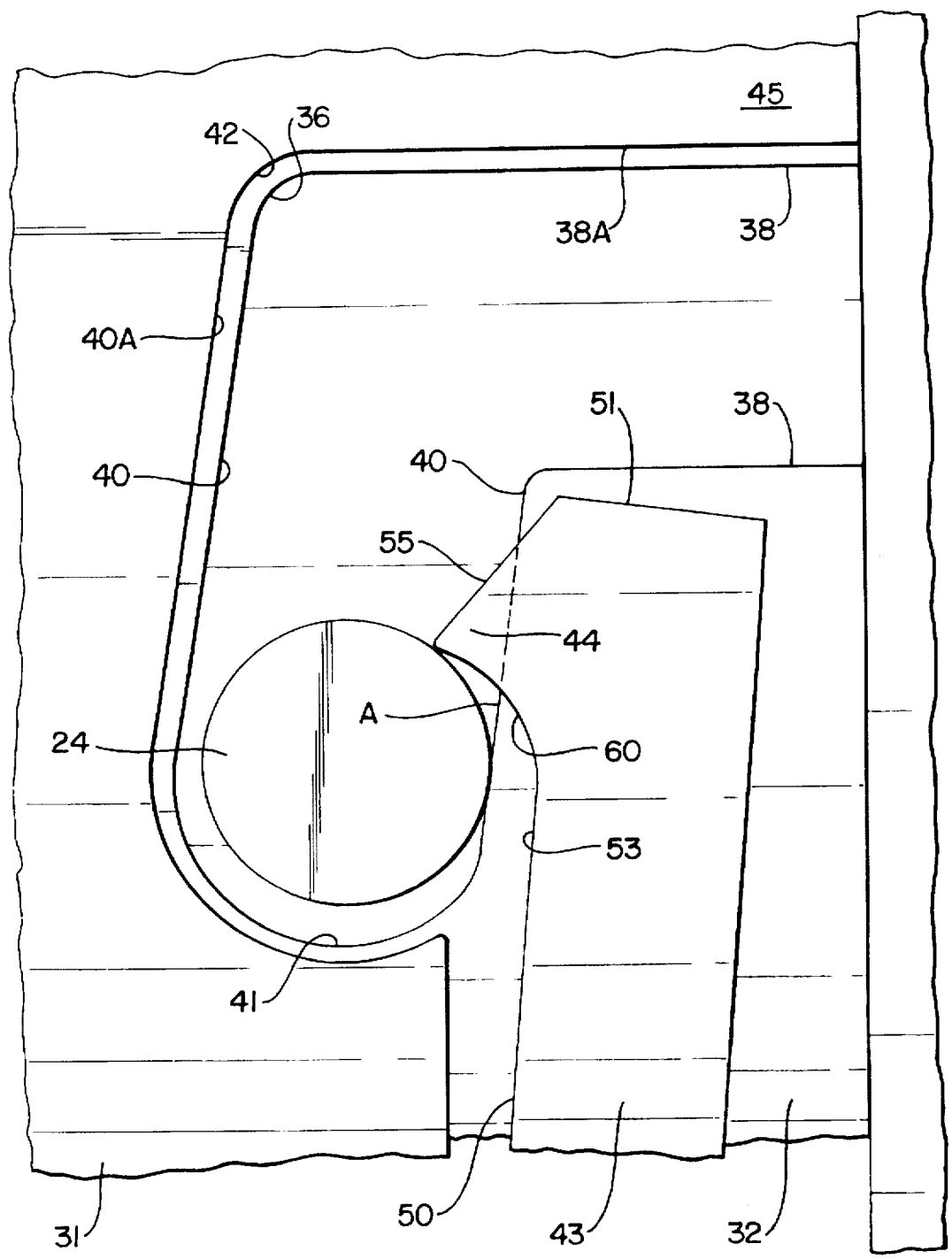
FIG. 7 is an enlarged view of the channels in the inner and outer sleeves and one engaging pin showing their position in a final state of attachment.

To attach a nose piece 14 onto the motor housing 12, the end surface 30 at the connecting end 15 of the nose piece 14 is placed in line with end 16 of the motor housing 12 in a rotational orientation so that the pins 22 and 24 are aligned with the openings of the channels 36 and 42 in the inner sleeve 32 and outer sleeve 31 as shown in FIGS. 3 and 6.

The motor housing 12 and nose piece 14 are brought together so that the tubular extension 20 of the motor housing 12 enters aperture 18 in the connecting end 15 of nose piece 14. These components are brought further together so that pins 22 and 24 enter the pairs of grooves 36 and 42 in the two sleeves 31 and 32. As the nose piece 14 and motor housing 12 continue to slide together, the pins 22 and 24 eventually reach junction between portions 38 and 40 of the channel 36 in the inner sleeve 32.

Figure 4:
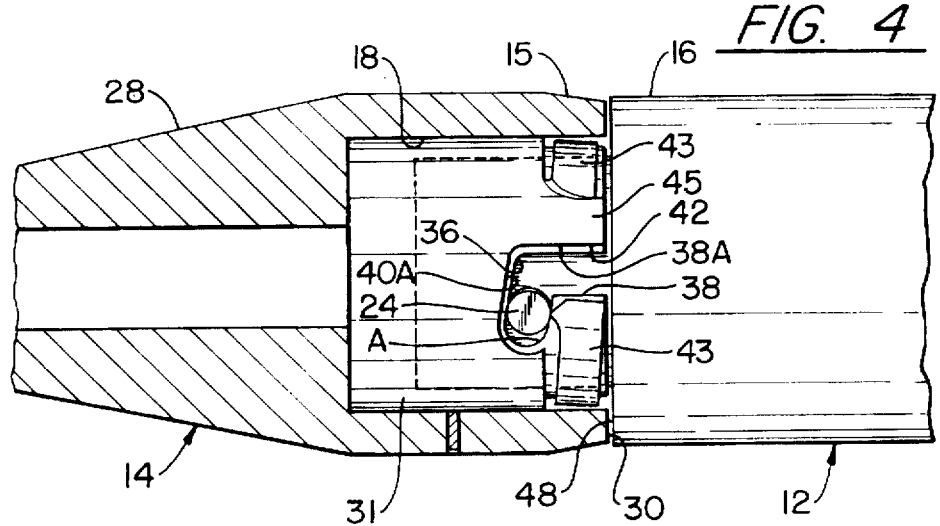
FIG. 4 is a view partially in section showing the nose piece and the motor housing in an intermediate state of attachment.
Figure 5:
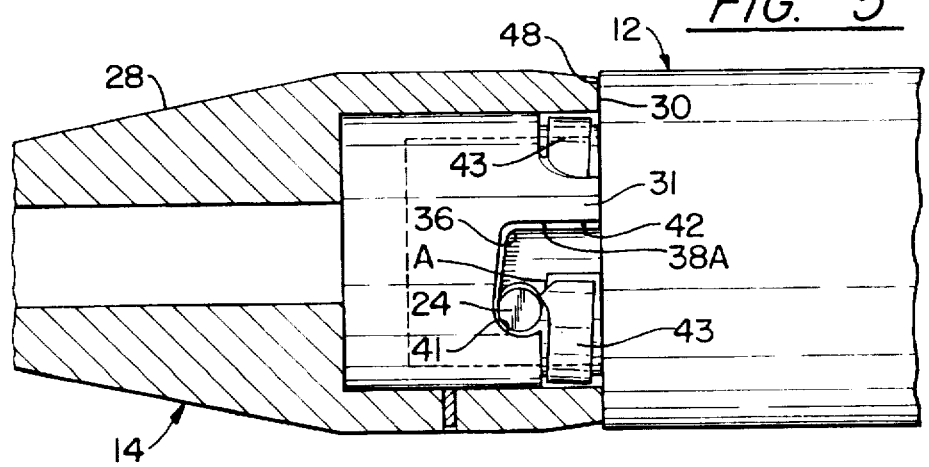
FIG. 5 is a view partially in section showing the nose piece and the motor housing in a final state of attachment.

When that position is felt by the user, the motor housing 12 and nose piece 14 are rotated with respect to one another so that the pins 22 and 24 move into the second portion 40 of each channel 36 in a direction toward each closed end 41. As that movement occurs, the pins 22 and 24 each engage the inclined cam surfaces 55 of the triangular projections 44, one at the free end of each cantilevered arcuate spring arm 43. The continued rotation of the nose piece 14 with respect to the motor housing 12 causes the pins 22 and 24 to exert pressure against the cam surfaces 55 which bends the cantilevered arcuate spring arms 43 toward the motor housing 12, as shown in FIG. 4.

As the pins 22 and 24 continue to slide along the second portion 40 of each channel 36, the angling of the second channel portion 40 away from the end surface 30 providing the ramp A draws the nose piece 14 against the flange surface 48 on the motor housing 12. Further rotational movement between the nose piece 14 and the motor housing 12 causes the two pins 22 and 24 to move past the apex of the triangular projections 44 and become engaged by the top of the slightly curved holding surfaces 60. The spring action of each cantilevered arcuate spring arm 43 acts against its cooperating pin through the top of the curved holding surface 60 to bias the bayonet connection to its connected position. The movement of the pins 22 and 24 in the channel portions 40 continues until the pins 22 and 24 become fully wedged against the ramp A of each of the channel portions 40 of the inner sleeve 32, pressing the end surface 30 of nose piece 14 against the flange surface 48 of the motor housing 12. The nose piece 14 becomes wedged before the pins 22 and 24 reach the closed ends 41 of the channels 36. In the wedged state, the force exerted by the cantilevered arcuate spring arms 43 through the top of the curved holding surfaces 60 of triangular projections 44 retains the pins 22 and 24 in the channels. This engagement firmly holds the nose piece 14 on the end of the motor housing 12 with the end surface 30 of the nose piece abutting the flange surface 48 on the motor housing.

Repeated replacement of a nose piece 14 on the end of the motor housing 12 produces wear of pins 22 and 24 decreasing their diameter and also causes enlargment of the channels 36 in the nose piece 14. However, the present fastening mechanism compensates for such wear and provides a secure attachment of the nose piece 14 to the motor housing 12. As the channels 36 enlarge and the pins 22 and 24 decrease in diameter, the pins travel farther into the second portion 40 of each channel 36 before the pins become wedged against ramps A to properly connect the nose piece 14 against the motor housing 12. However, the top of the curved holding surfaces 60 of the triangular projections 44 on the cantilevered arcuate spring arms 43 still engage the pins 22 and 24 to urge them into the wedged position. Thus, the angling of second channel portions 40 away from nose piece connecting end surface 30, and cantilevered arcuate spring arms 43 provide a self-compensating mechanism for wear of components of the bayonet connector assembly. The normal useful life of a typical nose piece 14 will expire when the component wear has progressed to a point where the pins 22 and 24 are able to reach the closed end 41 of each channel 36 and not have each pin 22 and 24 acted upon by its cooperating curved surface 60, but merely received in its matching curved surface 60.

When one attaches a nose piece 14 to a motor housing 12 for use by a surgeon, the joint is brought together and upon final positioning, it is bent to see if there is any movement between the nose piece 14 and motor housing 12. Movement indicates the connection should be inspected to place it in original condition.

Although specific embodiments of the invention have been set forth with a relatively high degree of particularity, it is intended that the scope of the invention not be so limited. Instead, the proper scope of the invention may include alternatives which are now within the purview of one skilled in the art. Thus, the scope should be ascertained by a reading of the claims to follow.

We claim:

1. A bayonet-type connector between two members, one member having a cylindrical projection extending from a flat surface, a second member having an aperture with a flat end surface for receiving said cylindrical projection, said cylindrical projection having diametrically opposed pins spaced from said flat surface, a first sleeve in said aperture having diametrically opposed guide channels for guiding said pins to a position where said flat end surface is wedged against said flat surface, a second sleeve in said aperture having spring arms for acting on said pins in said channels to bias said flat surface and said flat end surface together.

2. A bayonet-type connector as set forth in claim 1 wherein said spring arms are cantilevered arcuate spring arms, one cantilevered spring arm engaging each pin to bias said flat surface and said flat end surface together.

3. A bayonet-type connector as set forth in claim 2 wherein each cantilevered arcuate spring arm has a projection extending over a cooperating guide channel for acting against a pin.

4. A bayonet-type connector as set forth in claim 3 wherein said first sleeve is positioned within said second sleeve.

5. A bayonet-type connector as set forth in claim 3 wherein each projection is a triangular projection, each triangular projection having a first flat side and a second curved side, when said one member and second member are brought together said first flat side is engaged by its cooperating pin for placing each cantilevered arcuate spring arm in a position for said second curved side to act on its cooperating pin to bias said flat surface and said flat end surface together.

6. A bayonet-type connector as set forth in claim 2 wherein each cantilevered arcuate spring arm is mounted to move in an axial direction for biasing a pin in its cooperating channel to force said flat surface and said flat end surface together.

7. A bayonet-type connector as set forth in claim 6 wherein each cantilevered arcuate spring arm has a projection that extends over a cooperating guide channel for acting against a pin.

8. A bayonet-type connector as set forth in claim 1 wherein said second sleeve has a tight fit in said aperture, and said first sleeve has a tight fit in said second sleeve.

9. A bayonet-type connector as set forth in claim 8 wherein each spring arm moves axially between said aperture and said first sleeve, said spring arms being thinner than the rest of the second sleeve to permit the spring arms to move freely.

10. A surgical instrument comprising:
 a motor housing having a cylindrical member with a radially projecting first pin, and having a flange surface which extends outwardly from the cylindrical member and is spaced from the first pin;
 a nose piece having an end with an aperture having a flat end surface therearound which receives the cylindrical member, and the aperture having a channel within which the first pin slides so that said flange surface and flat end surface engage each other, wherein the channel has an open end, said nose piece including a cantilevered spring arm for urging the first pin along the channel to force said flange surface and flat end surface together and retain the first pin in the channel;

wherein said nose piece comprises:

a first tubular sleeve within the aperture of said nose piece and having a first end, said first tubular sleeve having a first channel formed by a first portion which extends inwardly from the first end and having a second portion extending circumferentially from the first portion, and the cantilevered spring arm is formed between the second portion of the first channel and the first end;

a second tubular sleeve located within the aperture of said nose piece and having a second end, said second tubular sleeve having a second channel formed by a first portion extending inwardly from the second end and a second portion extending circumferentially at an angle inwardly from the first portion; and wherein one of the first tubular sleeve and second tubular sleeve is within the other one of the first tubular sleeve and second tubular sleeve, and the first channel being substantially aligned with the second channel.

11. The surgical instrument as recited in claim 10 wherein the second tubular sleeve is within the first tubular sleeve.

12. The surgical instrument as recited in claim 10 wherein:

said motor housing has a second pin extending radially from the cylindrical member;

said first tubular sleeve further includes a third channel formed by a third portion that extends inwardly from the first end and a fourth portion that extends circumferentially from the third portion, and including another cantilevered spring arm formed between the fourth portion of the third channel and the first end; and said second tubular sleeve further includes a fourth channel formed by a third portion extending inwardly from the second end and a fourth portion extending circumferentially from the third portion, wherein the third channel is substantially aligned with the fourth channel.

13. The surgical instrument as recited in claim 10 wherein the second portion of the second channel extends at an obtuse angle from the first portion.

14. The surgical instrument as recited in claim 10 wherein the cantilevered spring arm has a triangular projection projecting therefrom and extending over said first channel for engaging the first pin to urge the first pin along the first channel and retain the first pin in the first channel.

* * * * *